United States Patent [19]

Takamura

[11] Patent Number: 5,665,068
[45] Date of Patent: Sep. 9, 1997

[54] DUAL CHAMBER PREFILLABLE SYRINGE

[75] Inventor: Noriyuki Takamura, Iwaki, Japan

[73] Assignee: Arte Corporation, Tokyo, Japan

[21] Appl. No.: 509,732

[22] Filed: Aug. 1, 1995

Related U.S. Application Data

[63] Continuation of Ser. No. 200,567, Feb. 22, 1994, abandoned, which is a continuation of Ser. No. 885,978, May 20, 1992, abandoned.

[30] Foreign Application Priority Data

Jun. 26, 1991 [JP] Japan ................... 3-057218

[51] Int. Cl.⁶ ................... A61M 37/00
[52] U.S. Cl. ................... 604/90; 604/191; 604/416; 206/221
[58] Field of Search ................... 604/82–92, 191, 604/187, 207, 208, 211, 224, 240, 243, 241, 192, 234, 232, 218, 403, 416, 903; 222/136, 129; 206/219, 220, 221; 215/DIG. 3, DIG. 8

[56] References Cited

U.S. PATENT DOCUMENTS

| | | | |
|---|---|---|---|
| 3,075,525 | 1/1963 | McConnaughey | 604/89 |
| 3,330,280 | 7/1967 | Ogle | 604/89 |
| 3,348,546 | 10/1967 | Roberts et al. | 604/89 |
| 3,351,058 | 11/1967 | Webb | 604/90 |
| 3,543,967 | 12/1970 | O'Connor | 222/136 |
| 4,159,570 | 7/1979 | Buskas et al. | 604/87 |
| 4,226,236 | 10/1980 | Genese | 604/89 |
| 4,254,768 | 3/1981 | Ty | |
| 4,599,082 | 7/1986 | Grimard | |
| 4,613,326 | 9/1986 | Szware | |
| 4,792,329 | 12/1988 | Schreuder | |

FOREIGN PATENT DOCUMENTS

| | | |
|---|---|---|
| 1099362 | 9/1955 | France . |
| 49-14465 | 4/1974 | Japan . |
| 62-5357 | 1/1987 | Japan . |
| 88/02265 | 4/1988 | WIPO . |

Primary Examiner—Corrine M. McDermott
Assistant Examiner—Ronald K. Stright, Jr.
Attorney, Agent, or Firm—Oliff & Berridge

[57] ABSTRACT

A syringe outer cylinder is split into a front chamber outer cylinder and a rear chamber outer cylinder. Powdered medicine is sealed in a sterilized state in the front chamber outer cylinder. Liquid medicine is sealed in a sterilized state in the rear chamber outer cylinder. Thereafter, the front chamber outer cylinder is coupled to the rear chamber outer cylinder with a coupling component, and the dual chamber prefillable syringe is assembled. Therefore, sealing of powdered medicine and liquid medicine can occur in parallel.

8 Claims, 12 Drawing Sheets

Prior Art

Prior Art

Prior Art

DUAL CHAMBER PREFILLABLE SYRINGE

This is a Continuation of application Ser. No. 08/200,567 filed Feb. 22, 1994, now abandoned, which is a Continuation of application Ser. No. 07/885,978 filed May 20, 1992 now abandoned.

BACKGROUND OF THE INVENTION

This invention relates to improvements in a dual chamber prefillable syringe, in which predetermined quantities of first and second medicines are liquid-tightly partitioned in a syringe outer cylinder, in a sterilized state, for injection of both the medicines into a mixture in one chamber as a parenteral solution.

Unstable medicine that cannot be stocked as a parenteral solution is generally powdered by lyophilizing in a freeze-drying apparatus. The powdered medicine and a liquid medicine solution for dissolving the powdered medicine are sealed in a sterilized state and stocked, subsequently mixed for injecting, and used as a parenteral solution.

When powdered medicine and liquid medicine are used, a predetermined quantity of liquid medicine sealed in an ampule or a vial is first sucked into a syringe by a syringe needle. Then, the needle is pierced into a rubber plug of a vial in which a predetermined powdered medicine is sealed. The liquid medicine in the syringe is poured into the vial to mix the powdered medicine with the liquid medicine, creating a parenteral solution. The parenteral solution is again sucked into the syringe, the needle is removed from the rubber plug of the vial, and the solution is injected into a patient as it is.

However, this operation is complicated, taking much time. There is a danger of imparting pain to the patient at the time of injecting, due to the slight deformation of the end of the needle pierced into the rubber plug of the vial at the time of piercing. Further, there is also a danger that part of the rubber plug of the vial may be cut out by a syringe needle as finely pulverized rubber pieces which are, in turn, introduced into the needle and hence injected together with parenteral solution into a patient. The needle and/or the parenteral solution may also be contaminated with bacteria and foreign matters in the-atmosphere that are adhered to the rubber plug.

In order to eliminate the above dangers, there has been invented a conventional dual chamber prefillable syringe in which predetermined quantities of powdered medicine and liquid medicine are liquid-tightly partitioned in one syringe in a sterilized state.

As conventional dual chamber prefillable syringes, those of Japanese Utility Model Publication No. 49-14465, FIG. 19, and Japanese Patent Application Laid-open No. 625357, FIG. 20, are known. As shown in FIGS. 19 and 20, in both the dual chamber prefillable syringes, bypass grooves $1c$, $2c$ are recessed on the inner walls $1b$, $2b$, substantially at the longitudinal centers of syringe outer cylinders $1a$, $2a$. Sealing plugs $1f$, $2f$, having smaller thicknesses $1e$, $2e$ than the lengths $1d$, $2d$ of the bypass grooves $1c$, $2c$, are liquid-tightly engaged at positions near outer cylinder openings $1g$, $2g$ in the syringe outer cylinders $1a$, $2a$. First inner chambers $1j$, $2j$ are formed between the cylinder ends $1i$, $2i$, liquid-tightly sealed by a sealing plug h or a stopper t, and the sealing plugs $1f$, $2f$. Plungers $1k$, $2k$ are liquid-tightly engaged at positions near the outer cylinder openings $1g$, $2g$ to form second inner chambers $1m$, $2m$ between the plungers $1k$, $2k$ and the sealing plugs $1f$, $2f$.

Since the dual chamber prefillable syringes shown in FIGS. 19 and 20 are constructed in the same configurations as described above, the following prior art will be described with reference to the dual chamber prefillable syringe shown in FIG. 19.

The dual chamber prefillable syringe of FIG. 21 has powdered medicine of a predetermined quantity sealed in a sterilized state in the first inner chamber $1j$ and liquid medicine of a predetermined quantity sealed in a sterilized state in a second inner chamber $1m$. When used, the plunger $1k$ is pushed forward by a syringe inner cylinder n to raise the hydraulic pressure of the liquid medicine, thereby pressing forward the sealing plug $1f$ to the bypass groove $1c$ in the side of the syringe outer cylinder $1a$ by means of the raised hydraulic pressure. When the plug $1f$ is thus pressed, and introduced into the region of the bypass groove $1c$, the first inner chamber $1j$ communicates with the second inner chamber $1m$ so that the inner pressures in both the inner chambers $1j$ and $1m$ become uniform, and the plug $1f$ is hence stopped. When the plunger $1k$ is further pressed by the syringe inner cylinder n, the liquid medicine is fed into the first inner chamber $1j$ through the bypass groove $1c$, as indicated by an arrow y in FIG. 21. As the plunger $1k$ contacts the plug $1f$, the entire liquid medicine is fed into the first inner chamber $1j$, and the liquid medicine is mixed with the powdered medicine in the first inner chamber $1j$ to produce a parenteral solution.

Since both the powdered medicine and the liquid medicine are filled in advance and sealed in the syringe outer cylinder $1a$, they are not contaminated with bacteria, etc., when injected into a patent as a parenteral solution. Therefore, it is best if the powdered medicine is sealed in the first inner chamber $1j$, the liquid medicine is sealed in the second inner chamber $1m$, and the dual chamber prefillable syringe containing both the powdered and liquid medicines is heated, to be sterilized, by high pressure steam, etc. This simultaneously sterilizes both the powdered and liquid medicines. If the powdered medicine is heat treated, however, its physical properties are varied. Therefore, it is impossible to heat-sterilize the dual chamber prefillable syringe when both the powdered and liquid medicines are partitioned and filled.

Therefore, in the conventional dual chamber prefillable syringe, liquid medicine is filled in a sterilized state in the syringe outer cylinder $1a$, medicine liquid is freeze-dried to powdered medicine by a freeze-drying apparatus and held therein in a sterilized state. The sealing plug $1f$ is engaged at a position near the outer cylinder opening $1g$ from the bypass groove $1c$ in the syringe outer cylinder $1a$ while the syringe is in the freeze-drying apparatus to seal the powdered medicine in a sterilized state in the first inner chamber $1j$ in the syringe outer cylinder $1a$. Thereafter, as shown in FIG. 22, liquid medicine q is transferred from a sterilized sealed vessel, through a pouring pipe p, into the syringe outer cylinder $1a$, while powdered medicine s is sealed in a sterilized state in the first inner chamber $1j$. The plunger $1k$ is subsequently sealed at a position near the outer cylinder opening $1g$ in the syringe outer cylinder $1a$, sealing the liquid medicine q in a sterilized state in the second inner chamber $1m$ in the syringe outer cylinder $1a$.

The filling and sealing of the liquid medicine q in the syringe outer cylinder $1a$, in which the powdered medicine s is sealed in a sterilized state, is conducted under a sterilized environment, but the working steps are considerably long. Therefore, there has been a danger of contamination of bacteria, etc. of the liquid medicine q, the powdered medicine s and the syringe outer cylinder $1a$ during the filling and sealing of the conventional dual chamber prefillable syringe.

As described above, the powdered medicine s is sealed in the sterilized state in the first inner chamber $1j$ in the syringe outer cylinder 1a. To achieve this, after the liquid medicine to be used as powdered medicine s of a predetermined quantity is filled in a sterilized environment in the syringe outer cylinder 1a, a freeze-drying process occurs. The liquid medicine is changed to powdered medicine s in a freeze-drying apparatus, in a sterilized environment. A sealing process inserts a sealing plug 1f into the syringe outer cylinder 1a, at a position near the outer cylinder opening 1g, via the bypass groove 1c, by an insertion rod set in the freeze-drying apparatus.

Since it takes 20 hours or longer to carry out the freeze-drying process in the freeze-drying apparatus (conducting both the freeze-drying process and the sealing process), it is important to improve the production efficiency of the process. In order to improve the production efficiency of the freeze-drying process, it is required to set as many syringe outer cylinders 1a as possible, sealed at the cylinder ends, in the freeze-drying apparatus.

However, since the conventional syringe outer cylinder 1a is long, the number of the syringe outer cylinders 1a to be set in the freeze-drying apparatus is limited. Since the sealing position of the sealing plug 1f is disposed substantially at the center of the outer cylinder 1a, the insertion rod u for inserting the sealing plug if to the sealing position becomes long, as shown in FIG. 23, and the space in the freeze-drying apparatus occupied by the insertion rod u is increased. Hence, there is a problem in that the number of the outer cylinders 1a to be set in the freeze-drying apparatus is limited.

SUMMARY OF THE INVENTION

An object of this invention is to provide a dual chamber prefillable syringe that can achieve the following in view of the above-described problems of the prior art:

(a) When a predetermined quantity of powdered medicine is sealed in a sterilized state in a first inner chamber, and a predetermined quantity of liquid medicine for dissolving the powdered medicine is sealed in a sterilized state in a second inner chamber, the parallel process of sealing the powdered medicine and the liquid medicine is performed. Filling and sealing of the liquid medicine in a syringe outer cylinder after the powdered medicine is sealed in a sterilized state are eliminated. A dangerous situation, in which the powdered medicine, the liquid medicine and the syringe outer cylinder are contaminated with bacteria, etc., during the process, is eliminated.

(b) Increasing the number of syringe outer cylinders to be set in a freeze-drying apparatus to improve production efficiency of the freeze-drying work.

In order to solve the above-described problems, this invention provides a dual chamber prefillable syringe comprising: a syringe outer cylinder having a bypass groove longitudinally recessed on an inner wall substantially at the center thereof and a cylindrical outer opening at one end thereof and a cylindrical end at an opposite end thereof; said syringe outer cylinder is split in a direction perpendicular to a longitudinal direction at a position between said bypass groove and said outer cylinder opening, dividing it into a front chamber outer cylinder and a rear chamber outer cylinder; said front chamber outer cylinder including said bypass groove, said cylindrical end and a first split opening; said rear chamber outer cylinder including said outer cylinder opening and a second split opening; an inner peripheral edge of said split opening being opposed over an entire periphery to an inner peripheral edge of said second split opening, so that said front chamber outer cylinder and said rear chamber outer cylinder are disposed in series; and said front chamber outer cylinder and said rear chamber outer cylinder being liquid-tightly held by a coupling component; thickness less than the length of said bypass groove and liquid-tightly sealed at a position near an said split opening to form a first inner chamber between a liquid-tightly sealed cylindrical end thereof and said sealing plug; and a plunger, liquid-tightly sealed at a position near said outer cylinder opening, to form a second inner chamber between said plunger and said sealing plug.

The following structures are added to the constitution of this invention:

(A) The sealing plug is formed of one piece.

(B) The sealing plug comprises a first sealing plug and a second sealing plug by splitting the sealing plug in a direction perpendicular to a thickness direction. The first sealing plug is liquid-tightly sealed at a position near the first split opening in the front chamber outer cylinder. The second sealing plug is liquid-tightly sealed at a position near the second split opening of the rear chamber outer cylinder. A distance from an end face of said first sealing plug, at the bypass groove side, to an end face of said second sealing plug, at the outer cylinder opening side, is set shorter than the length of said bypass groove.

(C) The dual chamber prefillable syringe further comprises a needle mounting cylinder including a base cylinder and an end cylinder, a bottomed hollow guard, and a bottomed hollow sealing plug made of an elastic material. The cylindrical end of the front chamber outer cylinder is formed in a wide port bottle shape. The bottomed hollow sealing plug is sealed in said cylindrical end in such a manner that a bottom of the bottomed hollow sealing plug faces the first inner chamber, so that said cylindrical end is liquid-tightly sealed. The base cylinder of the needle mounting cylinder is seated in the hollow section of said sealing plug. The end cylinder of the needle mounting cylinder protrudes from an end opening of said cylindrical end. An outer peripheral surface of the end cylinder is gradually reduced in diameter toward its end as a lure tapered surface. A cylindrical hole is perforated through the needle mounting cylinder from an end face of the end cylinder to an end face of said base cylinder. A guard base of the bottomed hollow guard is gas-tightly secured to an outer wall of said cylindrical end so that the end cylinder of said needle mounting cylinder is sealed in said guard. A collapsible brittle portion is circumferentially formed at a position of widest diameter of said lure tapered surface.

(D) The dual chamber prefillable syringe further comprises a stopper made of an elastic material, a bottomed hollow end housing and a bottomed hollow elastic cap. The stopper is sealed in the cylindrical end of the front chamber outer cylinder to liquid-tightly seal said cylindrical end. A distance from the end opening of said cylindrical end to said stopper is longer than a distance from the bypass groove to an end face of the plunger at the bypass groove side. An end of the cylindrical end is gas-tightly engaged within the coupling portion of the bottomed hollow end housing so that a hollow section of said end housing, from the end opening of said cylindrical end to an inner surface of a bottom of said end housing, is formed as a bypass chamber. A length of said bypass chamber is set greater than a thickness of said stopper. The end opening is included in a surface contacting said bypass chamber. A plurality of bypasses are recessed longitudinally of said end housing on an inner wall of said end housing. A plurality of bottom grooves coupled to said bypass are recessed radially on an inner surface of the bottom of said end housing. A housing recess is formed at a portion having all the bottom grooves, to connect all the bottom grooves to said housing recess. A needle mounting portion is suspended from an outer surface of the bottom of said housing. A small hole, from an end of the needle mounting portion to said housing recess, is perforated through the needle mounting portion. The needle mounting portion is liquid-tightly sealed with the hollow section of the bottomed hollow cap.

Further, the following structures are applied to the structure as in the above paragraph (D) of this invention.

(E) An outer wall surface of the needle mounting portion is gradually reduced in diameter toward its end as a lure tapered surface. An inner wall surface of the bottomed hollow cap is formed in the same tapered surface as said lure tapered surface.

(F) The dual chamber prefillable syringe further comprises a needle tube and a cap. The outer wall surface of the needle mounting portion is gradually reduced in diameter toward its end in a tapered surface. A base needle of the needle tube is perforated through, from the end of the small hole of the needle mounting portion to the housing recess, so that said base needle is gas-tightly secured to the small hole of the needle mounting portion. A needle hole perforated through said needle tube is connected to said housing recess. An end needle of said needle tube is provided to protrude from the needle mounting portion. The cap acts as a needle guard. A length of a hollow section of said needle guard is set longer than the total of the length of said end needle and the length of the needle mounting portion. An inner wall of said needle guard is formed in the same tapered surface as the tapered surface of the needle mounting portion. The end needle is sealed in the hollow section of said needle guard.

Further, the following structures are applied to the structure as in the above paragraph (E) of this invention.

(G) The dual chamber prefillable syringe further comprises a lure lock having a columnar portion. The lure lock is suspended from the outer surface of the housing bottom. The columnar portion includes the needle mounting portion therein. Female threads are formed on an inner peripheral surface of the columnar portion. A flange is formed on an outer wall surface of the cap. The flange is engaged by the female thread with said lure lock.

Since this invention is constituted as described above, when a predetermined quantity of the powdered medicine is sealed in a sterilized state in the first inner chamber, a predetermined quantity of the liquid medicine is sealed in a sterilized state in the second inner chamber, and the plunger is pressed forward in the syringe inner cylinder, the hydraulic pressure of the liquid medicine is raised by pressing forward the plunger, and the sealing plunger is pressed forward to the bypass groove by the raised hydraulic pressure of the liquid medicine. Thus, when the sealing plug falls within a range of the length of the bypass groove, the first inner chamber communicates with the second inner chamber through the bypass groove so that the pressures of both the first and second inner chambers become uniform, and hence the sealing plug is stopped at the bypass groove. Only the plunger is then continuously pressed forward to feed the liquid medicine into the first inner chamber. Then, the plunger contacts the sealing plug to feed the entire quantity of the liquid medicine into the first inner chamber. Thus, when the powdered medicine is mixed with the liquid medicine, a parenteral solution is produced. Therefore, since the sealing state of the powdered medicine and the liquid medicine is maintained even during the step of producing the parenteral solution by the above-described operation, there is no danger of contamination during the producing step.

Since this invention is constituted as described above, a predetermined quantity of powdered medicine can be sealed in a sterilized state in the front chamber outer cylinder by freeze-drying. Further, the step of sealing a predetermined quantity of the liquid medicine in the rear chamber outer cylinder, thermally sterilizing it, and sealing the liquid medicine in a sterilized state in the rear chamber outer cylinder, and the step of sealing the powdered medicine in a sterilized state in the front chamber outer cylinder, can be treated in parallel. Further, the front chamber outer cylinder is coupled in series with the rear chamber outer cylinder through the coupling component in a sterilized environment. More specifically, when a predetermined quantity of the powdered medicine is sealed in a sterilized state in the first inner chamber, and a predetermined quantity of the liquid medicine for dissolving the powdered medicine is sealed in a sterilized state in the second inner chamber, the sealing process of the powdered medicine and the liquid medicine can be treated in parallel. Thus, filling and sealing processes of the liquid medicine in the syringe outer cylinder after the powdered medicine has been sealed in a sterilized state are eliminated. Therefore, there is no danger of the liquid medicine, the powered medicine and the interior of the syringe outer cylinder being contaminated with bacteria, etc., during the filling and sealing processes.

Further, since this invention is constituted as described above, the length of the front chamber outer cylinder is shorter than that of the syringe outer cylinder of the conventional dual chamber prefillable syringe. In the sterilized freeze-drying apparatus, the split opening of the front chamber outer cylinder is sealed, and the powdered medicine can be sealed in a sterilized state in the front chamber outer cylinder. Therefore, in order to seal the powdered medicine in the freeze-drying apparatus, the length of the inserting rod set in the freeze-drying apparatus can be shortened, as compared with that of the conventional inserting rod. Accordingly, a space in the freeze-drying apparatus occupied by the inserting rod can be reduced. Further, the length of the front chamber outer cylinder is shortened, as compared with that of the conventional dual chamber prefillable syringe, and the number of the front chamber outer cylinders that can be set in the working space can be increased, as compared with the conventional dual chamber prefillable syringe. This improves the production efficiency of the freeze-drying work by the freeze-drying apparatus.

Since the structure as described in the above paragraph (A) is added to the constitution of this invention, even if the sealing plug, while assembling the dual chamber prefillable syringe, is deviated longitudinally of the syringe outer cylinder, the thickness of the sealing plug is not increased in the bypass groove, as in the case in which the sealing plug is split. Therefore, since the sealing plug reliably falls in a range of the length of the bypass groove, the first inner chamber can effectively communicate with the second inner chamber, and assembly is facilitated.

Since the structure as described in the above paragraph (B) is employed in the constitution of this invention, the medicine liquid filled in the front chamber outer cylinder can be freeze-dried into powdered medicine by the freeze-drying apparatus and the powdered medicine can be sealed in a sterilized state in the front chamber outer cylinder, between the sealing plunger and the cylindrical end. The liquid medicine can be sealed in the rear chamber outer cylinder between the sealed plug and the plunger, sterilized and sealed in advance, in a sterilized state, in the rear chamber outer cylinder. Therefore, the powdered medicine in the front chamber outer cylinder remains sealed in a sterilized state, the liquid medicine in the rear chamber outer cylinder also remains sealed in a sterilized state, and the dual chamber prefillable syringe can be assembled. Therefore, entry of bacteria in the powdered medicine in the front chamber outer cylinder and the liquid medicine in the rear chamber outer cylinder can be prevented, and danger is reduced.

Since the distance from the end face of the sealing plug, at the bypass groove side, to the end face of the sealing plug at the outer cylinder opening side is set shorter than the length of the bypass groove, the first inner chamber reliably communicates with the second inner chamber when the plunger is pressed forward to press the sealing plug to the bypass groove. Therefore, the liquid medicine in the second inner chamber can be fed into the first inner chamber, to mix the powdered medicine with the liquid medicine in the first inner chamber, thereby producing parenteral solution.

Since the structure described in the above paragraph (C) is employed in the constitution of this invention, the end cylinder of the needle mounting cylinder can be sealed in a sterilized state, such as by heating, before the powdered medicine is sealed in the front chamber outer cylinder. For injection, side pressure is applied to the guard by a finger to break the guard at the collapsible brittle portion to expose the end cylinder, thereby mounting a syringe needle on the lure tapered surface of the end cylinder. Therefore, the syringe needle can be easily mounted, and the end cylinder is held in a sterilized state up to the time of injection.

Since the structure described in the above paragraph (D) is employed in the constitution of this invention, the needle mounting portion can be held by the cap and sterilized, such as by-thermally sterilizing, before the powdered medicine is sealed in the front chamber outer cylinder. The interior of the small hole of the needle mounting portion, the bypass chamber and the interior of the front chamber outer cylinder, from the stopper to the end opening, can be sealed in the sterilized state.

When the powdered medicine is sealed in the first inner chamber and the liquid medicine is sealed in the second inner chamber, the cap is removed and the plunger is pressed forward in the syringe inner cylinder. Then, the hydraulic pressure of the liquid medicine is raised by pressing the plunger forward, the sealing plug is pressed by the raised hydraulic pressure of the liquid medicine, and the air in the second inner chamber is compressed by pressing the sealing plug to raise the pneumatic pressure in the second inner chamber to press forward the stopper. But when the cap is removed, the bypass chamber in the end housing communicates with the atmosphere. Accordingly, even if the stopper is pressed, air in the bypasses escapes into the atmosphere and the internal pressure in the bypass chamber is not raised. Therefore, the sealing plug can be smoothly pressed forward to the bypass groove side.

When the plunger is subsequently pressed forward, the sealing plug is pressed to the region of the length of the bypass groove. The first inner chamber communicates with the second inner chamber through the bypass groove, the sealing plug is stopped and only the plunger is thereafter continuously pressed forward to feed the liquid medicine into the first inner chamber. The plunger then contacts the sealing plug when the entire quantity of the liquid medicine is fed into the first inner chamber, and the powdered medicine and the liquid medicine are mixed in the first inner chamber to produce a parenteral solution. In this case, the stopper is also pressed by pressing the plunger, but since the distance from the end opening of the front chamber outer cylinder to the stopper is set longer than the distance from the bypass groove to the end face of the plunger at the bypass groove side, the stopper is not pressed into the bypass chamber until the entire quantity of the liquid medicine is fed into the first inner chamber. After the parenteral solution is produced, the stopper is pressed into the bypass chamber. Thus, when the stopper is introduced into the bypass chamber, the stopper contacts the housing bottom, and the parenteral solution is fed from the bypasses of the inner wall of the housing to the bottom groove coupled to the bypasses, introduced to the housing recess coupled to the bottom groove, further fed through the small hole of the needle mounting portion perforated to the recess, and fed externally of the dual chamber prefillable syringe. The sealing plug thus contacts the stopper to externally press the entire quantity of the parenteral solution.

Since the structure described in the above paragraph (E) is added to the structure described in the above paragraph (D) in the constitution of this invention, it is easy to mount the syringe needle on the lure tapered surface of the needle mounting portion.

Since the structure described in the above paragraph (F) is added to the structure described in the above paragraph (D) in the constitution of this invention, mounting the syringe needle at the needle mounting portion is eliminated. Further, the needle mounting portion, the interior of the needle hole of the needle tube, the bypass chamber, the interior of the front chamber outer cylinder from the stopper to the end opening, and the end needle of the needle tube can be sealed, in a sterilized state, by the needle guard. Sterilizing, such as by thermally sterilizing, of the front chamber outer cylinder can be achieved before the powdered medicine is sealed in the front chamber outer cylinder. Further, the end needle of the needle tube is protected by the needle guard to prevent the deformation of the end of the end needle. Therefore, pain imparted to a patient at the time of injection, due to the deformation of the end of the end needle, can be eliminated.

Since the structure described in the above paragraph (G) is added to the structure described in the above paragraph (E) in the constitution of this invention, the sealing state of the needle mounting portion with the cap is held by engaging the flange of the cap with the female threads of the lure lock. Thus, there is no danger of cap removal from the needle mounting portion up to the time of injection. Therefore, the needle mounting portion, the interior of the small hole of the needle mounting portion, the bypass chamber and the interior of the front chamber outer cylinder, from the stopper to the end opening, are reliably held in a sterilized state by the cap up to the time of injection.

DESCRIPTION OF THE PREFERRED EMBODIMENTS

Figure 1:
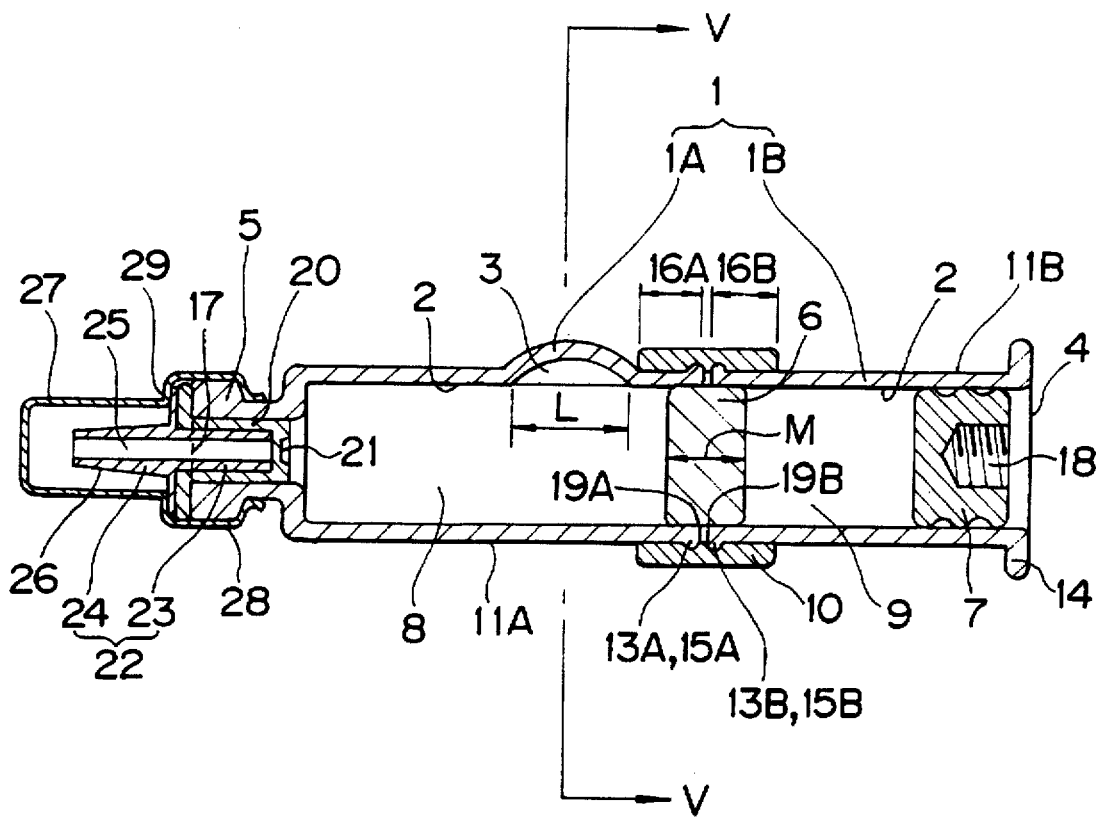
FIG. 1 is a longitudinal sectional view of a first embodiment according to the present invention.
Figure 2:
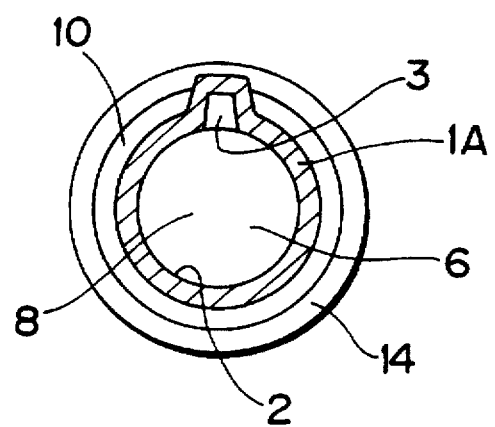
FIG. 2 is a sectional view taken along line V—V of FIG. 1.

The first embodiment of this invention will be described with reference to FIGS. 1 to 4 and FIG. 24.

A syringe outer cylinder 1 of a cylindrical shape, made of glass, is formed with a longitudinal bypass groove 3 on an inner wall 2, substantially at the center of the cylinder 1. The outer cylinder 1 is split in a direction perpendicular to the longitudinal direction, at a position between the bypass groove 3 and the outer cylinder opening 4, into a front chamber outer cylinder 1A and a rear chamber outer cylinder 1B. The front chamber outer cylinder 1A has bypass groove 3, a cylinder end 5 and a first split opening 12A. The rear chamber outer cylinder 1B has the outer cylinder opening 4 and a second split opening 12B. A protrusion 13A is circumferentially formed on an outer wall 11A of the front chamber outer cylinder 1A at the side of the split opening 12A. A protrusion 13B is circumferentially formed at the end of an outer wall 1ib of the rear chamber outer cylinder 1B at the side of the split opening 12B. An annular finger-grip 14 is circumferentially formed at the end of the outer cylinder opening 4. The front chamber outer cylinder 1A and the rear chamber outer cylinder 1B are disposed in series, oppositely to one another, over the entire peripheries of the inner peripheral edge 19A of the split opening 12A and the inner peripheral edge 19B of the split opening 12B. The front chamber outer cylinder 1A and the rear chamber outer cylinder 1B are coupled by a coupling component 10. The coupling component 10 is made of plastic and has elasticity and a cylindrical shape. The coupling component 10 is circumferentially formed with a recess 15A and a recess 15B, substantially at the center of the inner peripheral surface thereof, at a small interval. The protrusion 13A of the front chamber outer cylinder 1A is engaged with the recess 15A, and the protrusion 13B of the rear chamber outer cylinder 1B is engaged with the recess 15B, to liquid-tightly hold the coupling portion 16A of the front chamber outer cylinder 1A and the coupling portion 16B of the rear chamber outer cylinder 1B.

An integral sealing plug 6 is made of rubber and has a thickness M shorter than the length L of the bypass groove 3. The integral sealing plug 6 is liquid-tightly engaged within a position where the front chamber outer cylinder 1A and the rear chamber outer cylinder 1B are coupled to one another, so that both the split opening 12A and the split opening 12B are liquid-tightly sealed by the sealing plug 6. Thus, the first inner chamber 8 is formed within the front chamber outer cylinder 1A between the integral sealing plug 6 and end 5 closed with a sealing plug 20. A plunger 7 made of rubber is liquid-tightly sealed at a position near the outer cylinder opening 4 in the rear chamber outer cylinder 1B to form a second inner chamber 9 between the plunger 7 and the sealing plug 6. Female threads 18 are formed on the plunger 7 from the end face of the outer cylinder opening 4, so as to mount a syringe inner cylinder 30.

The end 5 of the front chamber outer cylinder 1A is formed in a wide port bottle shape. A bottom 21 of a bottomed hollow sealing plug 20 made of rubber is liquid-tightly engaged with an inner surface of the end 5 facing to the first inner chamber 8, so that the end 5 is liquid-tightly closed. A base cylinder 23 of a needle mounting cylinder 22 is sealed with the hollow section of the sealing plug 20. The mounting cylinder 22 protrudes from the end opening 17 of the end 5. A cylindrical hole 25 is perforated through from the end face of a tip 24 to the end face of the base cylinder 23. The outer peripheral surface of the tip 24 is gradually reduced in diameter toward the end as a luer tapered surface 26. A guard base 28 of a bottomed hollow guard 27 made of aluminum is gas-tightly secured to the outer peripheral surface of the end 5, by caulking. The tip 24 of the needle mounting cylinder 22 is sealed in the hollow section of the guard 27. A collapsible brittle portion 29 is circumferentially formed in the guard 27 at the largest diameter portion of the luer tapered surface 26 of the tip 24.

Since the end 5 of the front chamber outer cylinder 1A is constructed as described above, the tip 24, to be mounted with a syringe needle, can be reliably held in the guard 27, in a sterilized state, up to the time of injection. The front chamber outer cylinder 1A is sterilized, by heating, for example, before powdered medicine is sealed in the front chamber outer cylinder 1A.

In order to seal the powdered medicine in a sterilized state in the front chamber outer cylinder 1A, after the interior of the guard 27 is sterilized, a predetermined quantity of liquid medicine to be freeze-dried into powdered medicine is filled in the front chamber outer cylinder 1A. Then the front chamber outer cylinder 1A is set in a freeze-drying apparatus in a sterilized state and the medicine liquid is freeze-dried. A sealing rubber plug 37 having a ventilation groove 38 is inserted into the split opening 12A by an insertion rod 36 set in the apparatus. The split opening 12A is sealed by the sealing rubber plug 37 so that the powdered medicine is sealed in a sterilized state in the front chamber outer cylinder 1A.

Figure 23:
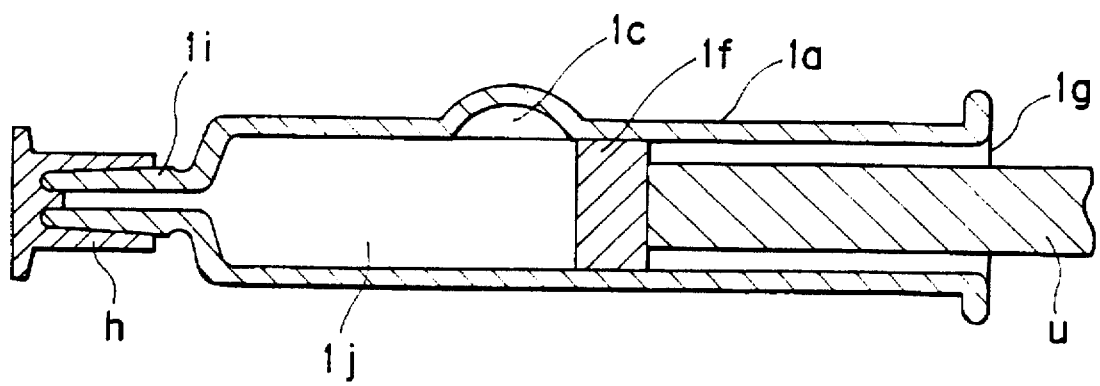
FIG. 23 is a longitudinal sectional view showing a sealing plunger inserted in the FIG. 19 device.
Figure 24:
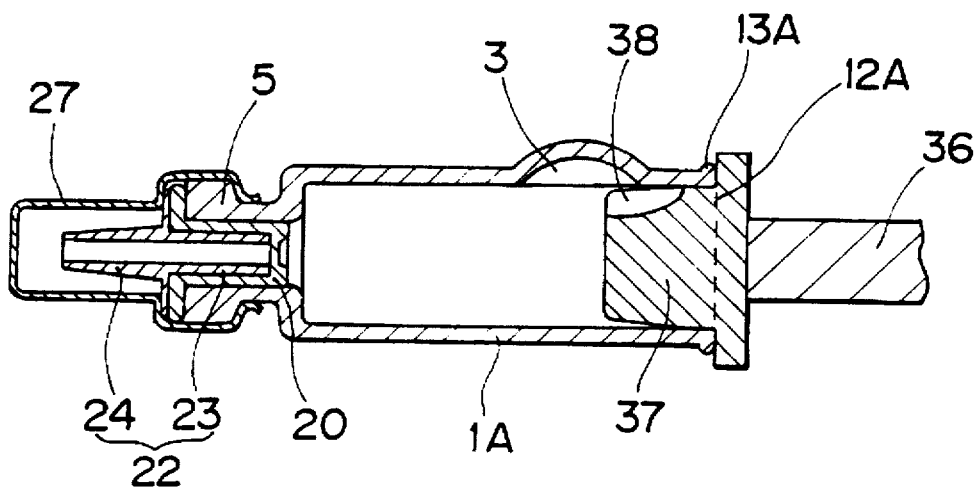
FIG. 24 is a longitudinal sectional view showing the sealing rubber plug in a front chamber outer cylinder of the FIG. 1 device.

As shown in FIG. 23, in a conventional dual chamber prefillable syringe, since a syringe outer cylinder 1a is formed of one piece, it is necessary to insert a sealing plug if substantially to the center of the outer cylinder 1a by an inserting rod u and to seal powdered medicine in a sterilized state in the outer cylinder 1a. Thus, the length of the conventional dual chamber prefillable syringe is increased due to the length of the rod u set in a freeze-drying apparatus. On the other hand, according to the dual chamber prefillable syringe as shown in FIG. 24, since the syringe outer cylinder 1 is split into the front chamber outer cylinder 1A and the rear chamber outer cylinder 1B, it is possible to seal the powdered medicine in a sterilized state in the front chamber outer cylinder 1A, by the sealing rubber plug 37. Therefore, the length of the inserting rod 36 can be shortened as compared with that of the conventional inserting rod u. Accordingly, the space in the freeze-drying apparatus occupied by the inserting rod 36 is reduced to increase the space for front chamber outer cylinder 1A. In addition, since the length of the front chamber outer cylinder 1A is shorter than that of the conventional syringe outer cylinder 1a, the number of the front chamber outer cylinders 1A that can be set in the freeze-drying apparatus is increased. Therefore, the production efficiency of the freeze-drying work by the freeze-drying apparatus can be improved.

In order to seal liquid medicine in a sterilized state in the rear chamber outer cylinder 1B, the coupling portion 16B of the rear chamber outer cylinder 1B is engaged with the coupling component 10 and recess 15B is engaged with protrusion 13B. The sealing plug 6 is sealed in the rear chamber outer cylinder 1B near the split opening 12B and a predetermined quantity of the liquid medicine is filled through the outer cylinder opening 4 into the rear chamber outer cylinder 1B. The plunger 7 is further sealed in the rear chamber outer cylinder 1B near the outer cylinder opening 4 to seal the liquid medicine between the sealing plug 6 and the plunger 7. Thereafter, the rear chamber outer cylinder 1B is sterilized by thermal sterilization, etc., to sterilize the liquid medicine sealed in the rear chamber outer cylinder 1B.

The front chamber outer cylinder 1A, in which the powdered medicine is sealed in a sterilized state, and the rear chamber outer cylinder 1B, in which the liquid medicine is sealed in a sterilized state, are assembled by removing the sealing rubber plug 37, contacting the rear chamber outer cylinder 1B at the coupling component 10 side with the coupling portion 16A of the front chamber outer cylinder 1A, coupling the front chamber outer cylinder 1A and the rear chamber outer cylinder 1B in series by the coupling component 10, and pressing the plunger 7 to move the sealing plug 6 to a position where the front chamber outer cylinder 1A and the rear chamber outer cylinder 1B are opposed to one another.

Figure 22:
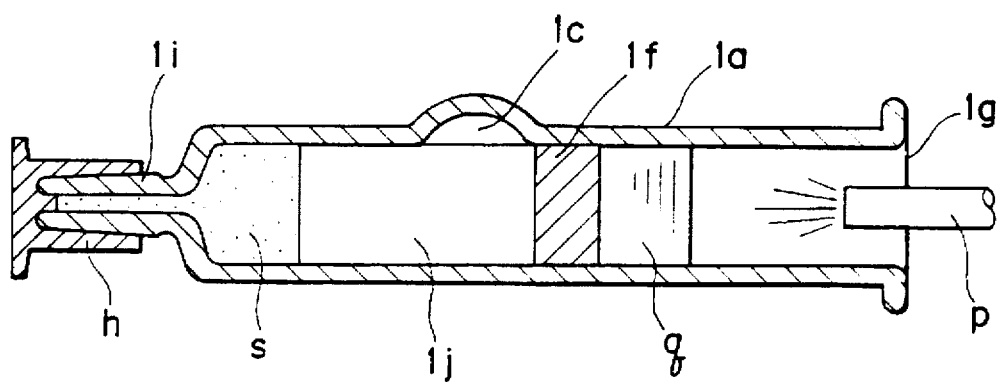
FIG. 22 is a longitudinal sectional view showing liquid medicine filling in the FIG. 19 device.

Since the outer cylinder 1a of the conventional dual chamber prefillable syringe shown in FIG. 22 is formed of one piece, it is necessary to seal powdered medicine s in the outer cylinder 1a in a sterilized state and to then fill and seal liquid medicine q in a sterilized environment in the outer cylinder 1a, which already includes the powdered medicine s. Therefore, as already described above, a danger exists that the liquid medicine q, the powdered medicine s and the interior of the syringe outer cylinder 1a are contaminated by the introduction of bacteria, etc., during filling and sealing work of the liquid medicine q even in the sterilized environment on the other hand, according to the present invention, since the syringe outer cylinder 1 is split into the front chamber outer cylinder 1A and the rear chamber outer cylinder 1B, the step of sealing a predetermined quantity of the powdered medicine in a sterilized state in the front chamber outer cylinder 1A and the step of sealing a predetermined quantity of liquid medicine in a sterilized state in the rear chamber outer cylinder 1B can be treated in parallel. Therefore, according to the present invention, it is not required to fill and seal the liquid medicine in the syringe outer cylinder 1, which already includes the powdered medicine. The danger of the liquid medicine, powdered medicine and the interior of the syringe outer cylinder 1 being contaminated by bacteria, etc., during the process is eliminated.

Figure 3:
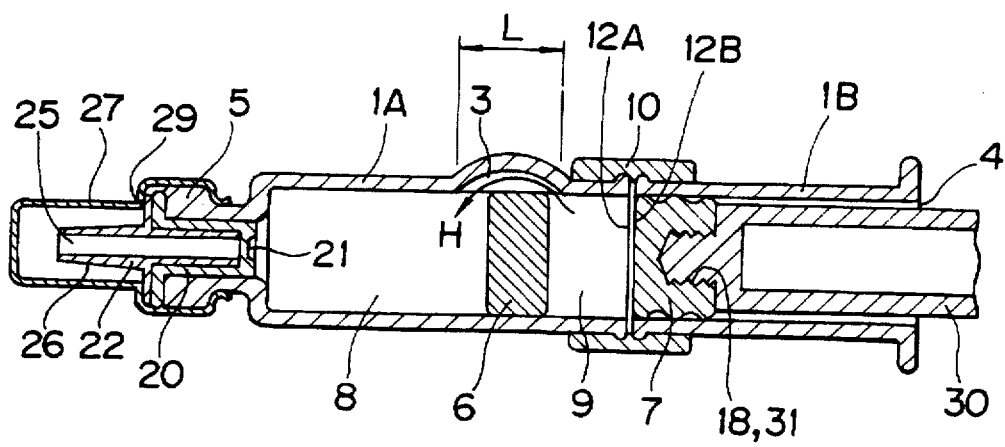
FIG. 3 is a longitudinal sectional view showing initial pressing of a plunger of the FIG. 1 device.
Figure 4:
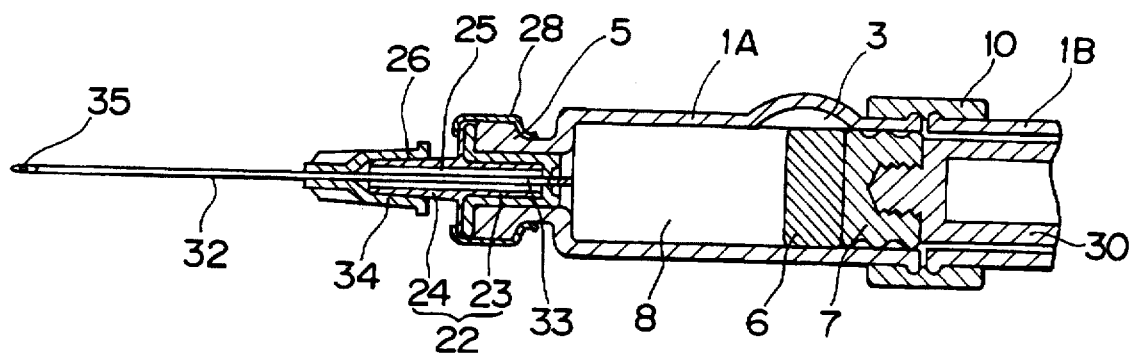
FIG. 4 is a partial longitudinal sectional view showing a double flank syringe needle mounted in the device of FIG. 1.

In the case of injection, male threads 31 of the syringe inner cylinder 30 are engaged with the female threads 18 of the plunger 7, and the inner cylinder 30 is mounted at the plunger 7, as shown in FIG. 3. The plunger 7 is pressed forwardly by the inner cylinder 30 so that the hydraulic pressure of the liquid medicine is raised and the sealing plug 6 is pressed forward to the bypass groove 3 side due to the increase in the hydraulic pressure. Thus, when the sealing plug 6 is introduced into a range of the length L of the bypass groove 3, the first inner chamber 8 communicates with the second inner chamber 9 through the bypass groove 3 so that the pressures in both the inner chambers 8 and 9 become uniform. Therefore, the sealing plug 6 is stopped. While the plunger 7 is then continuously pressed forward, the liquid medicine is, in turn, fed into the first inner chamber 8 as indicated by an arrow H until the plunger 7 contacts the sealing plug 6, thereby feeding the entire quantity of the liquid medicine into the first inner chamber 8. As a result, when the powdered medicine is mixed with the liquid medicine in the first inner chamber 8, a parenteral solution is produced. Thereafter, as shown in FIG. 4, a side pressure is applied to the guard 27 by a finger to break the guard 27 at the collapsible brittle portion 29 to expose the cylinder end 24. A short needle 33 of a double flank syringe needle 32 is introduced in the cylindrical hole 25 of the tip 24 and the needle base 34 of the double flank syringe needle 32 is mounted on the luer tapered surface 26 of the tip 24. The short needle 33 is pierced to the bottom 21 of the sealing plug 20 to bring a needle hole 35 of the double flank syringe needle 32 into communication with the first inner chamber 8.

In the embodiment described above, the sealing plug 6 is formed of one piece. Therefore, even if the sealing plug 6 deviates longitudinally relative to the syringe outer cylinder 1, when the dual chamber prefillable syringe is assembled, the thickness M of the sealing plug 6 is not greater than the length L of the bypass groove 3, as in the case in which the sealing plug 6 is split. Therefore, since the sealing plug 6 is always positioned within a range of the length L of the bypass groove 3, the first inner chamber 8 always communicates with the second inner chamber 9, and their assembly is facilitated.

Figure 5:
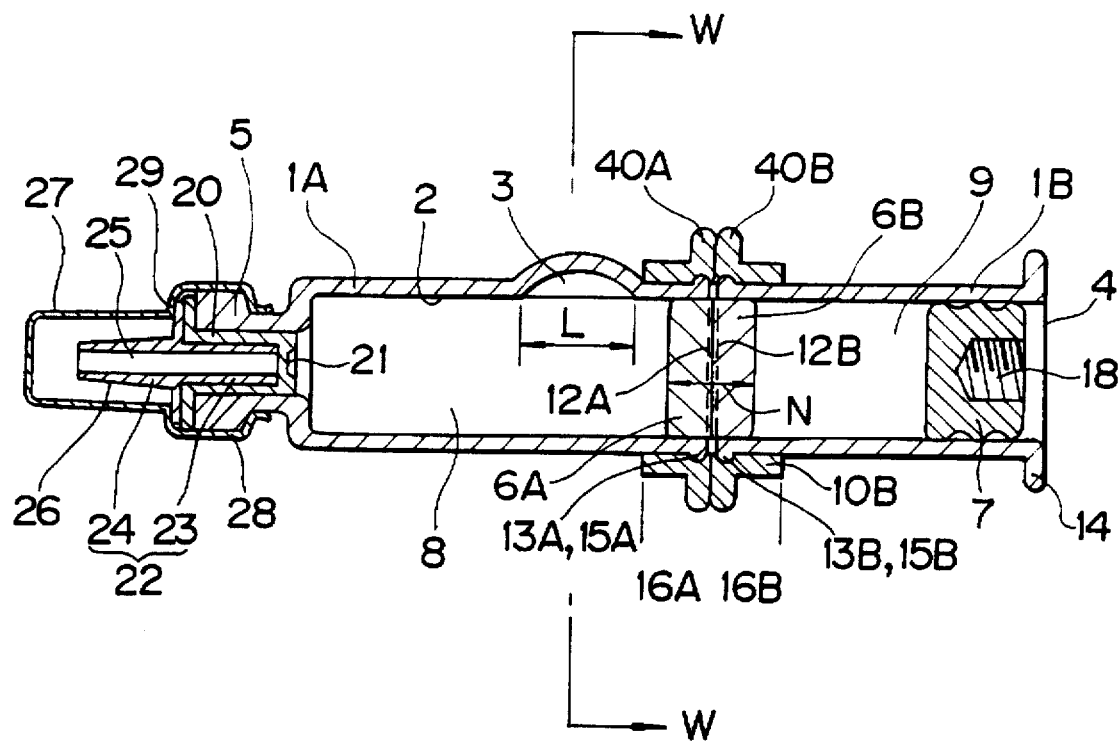
FIG. 5 is a longitudinal sectional view of a second embodiment according to the present invention.
Figure 6:
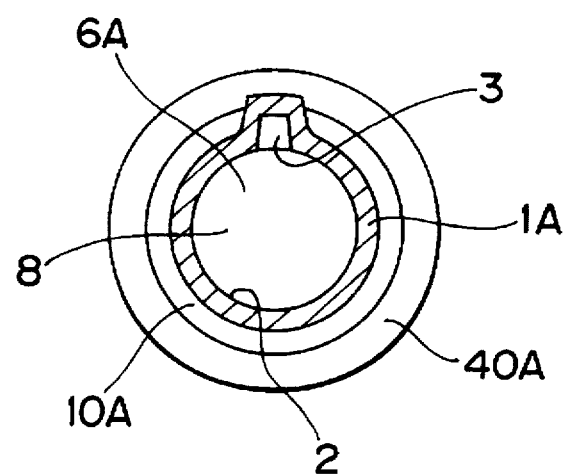
FIG. 6 is a sectional view take along line W—W of FIG. 5.

It is noted that the first embodiment according to the present invention is not limited in shape or materials to the particular shape and materials described above. In the embodiment described above, only one bypass groove 3 is employed. However, this invention is not limited to the particular embodiment. For example, the number of the bypass grooves 3 is not limited to only one, but may include a plurality of bypass grooves 3. Further, in the embodiment described above, the cylindrical coupling component 10 is formed of one piece. However, the coupling component 10 may be divided, as shown in the embodiments of FIGS. 5 and 6, as will be described later.

The second embodiment according to the present invention will be described with reference to FIGS. 5 and 6. However, in comparison with the first embodiment, the same device and components are denoted by the same reference numerals and symbols and only different structure, operation and effect will be described.

A sealing plug 6 is split in a direction perpendicular to a thickness direction, and divided into a first sealing plug 6A and a second sealing plug 6B. The sealing plugs 6A and 6B are contacted with each other in such a manner that sealing plug 6A is liquid-tightly positioned in a front chamber outer cylinder 1A near a split opening 12A and sealing plug 6B is liquid-tightly positioned in a rear chamber outer cylinder 1B near a split opening 12B. A distance N from the end face of the sealing plug 6A, near the end 5, to the end face of the sealing plug 6B, near the outer cylinder opening 4, is set shorter than the length L of a bypass groove 3.

A coupling component 10 is radially split and divided into a coupling component 10A and a coupling component 10B. An annular flange 40A is circumferentially formed on the outer peripheral surface of one axial end of the coupling component 10A, and a recess 15A is circumferentially formed on the inner peripheral surface near the end with the flange 40A. An annular flange 40B is circumferentially formed on the outer periphery of the one axial end of the coupling component 10B, and a recess 15B is circumferentially formed on the inner peripheral surface near the end with the flange 40B. A protrusion 13A of the front chamber outer cylinder 1A is engaged with the recess 15A of the coupling component 10A, and the coupling portion 16A of the front chamber outer cylinder 1A is liquid-tightly held by the coupling component 10A. A protrusion 13B of the rear chamber outer cylinder 1B is engaged with the recess 15B of the coupling component 10B, and coupling portion 16B of the rear chamber outer cylinder 1B is liquid-tightly held by the coupling component 10B. The flange 40A of the coupling component 10A is liquid-tightly adhered oppositely to the flange 40B of the coupling component 10B.

In the embodiment shown in FIG. 5, in order to seal powdered medicine in a sterilized state in the front chamber outer cylinder 1A, the front chamber outer cylinder 1A is sealed with the coupling component 10A, recess 15A engaging protrusion 13A, and the front chamber outer cylinder 1A is sterilized by sterilization (e.g. thermal) to sterilize the interior of the guard 27. Then, a predetermined quantity of medicine liquid to be freeze-dried into powdered medicine is filled in the front chamber outer cylinder 1A, the outer cylinder 1A is set within a freeze-drying apparatus of sterilized state, and the medicine liquid is freeze-dried into powdered medicine. The sealing plug 6A is subsequently inserted through the split opening 12A by an inserting rod set in the freeze-drying apparatus, and the split opening 12A is sealed by the sealing plug 6A, sealing the powdered medicine in a sterilized state in the front chamber outer cylinder 1A.

In order to seal the liquid medicine in a sterilized state in the rear chamber outer cylinder 1B, the rear chamber outer cylinder 1B is sealed with the coupling component 10B so that recess 15B engages protrusion 13B, and the split opening 12B is sealed with the sealing plug 6B. A predetermined quantity of liquid medicine is filled through the outer cylinder opening 4 into the rear chamber outer cylinder 1B. The plunger 7 is sealed in the rear chamber outer cylinder 1B near the outer cylinder opening 4, and the liquid medicine is sealed in the rear chamber outer cylinder 1B between the sealing plug 6B and the plunger 7. Thereafter, the rear chamber outer cylinder 1B is sterilized by sterilization (e.g. heating) to seal the liquid medicine in a sterilized state in the rear chamber outer cylinder 1B.

Then, the flange 40A of the coupling component 10A is liquid-tightly adhered oppositely to the flange 40B of the coupling component 10B in a sterilized environment so that the front chamber outer cylinder 1A and the rear chamber outer cylinder 1B are coupled in series with one another.

According to this embodiment, the sealing state in the front chamber outer cylinder 1A is not opened during the assembly process as in the first embodiment shown in FIG. 1. Therefore, the invasion of bacteria, etc. into the powdered medicine in the front chamber outer cylinder 1 is reliably prevented, and the danger of contaminating the powdered medicine by bacteria, etc., during assembly is greatly reduced.

In the embodiment shown in FIGS. 5 and 6, the sealing plug 6A contacts the sealing plug 6B. However, it is noted that, if a distance N between the sealing plug 6A and the sealing plug 6B falls within a shorter range than the length L of the bypass groove 3, the sealing plug 6A and the sealing plug 6B may be separated. In the embodiment shown in FIGS. 5 and 6, the coupling component 10 is split radially. However, the splitting direction of the coupling component 10 may be axial, and the number of divisions is not limited to two. Further, a method of coupling the split coupling component 10A to the coupling component 10B is not limited to the above-described adhering method, but may be a method of thermal fusion-bonding.

The third embodiment according to the present invention will be described with reference to FIGS. 7 to 10. In comparison with the first embodiment as shown in FIGS. 1 to 4, the same device and components are denoted by the same reference numerals and symbols, and only different structure, operation and effect will be described.

A cylindrical end 5 of a front chamber outer cylinder 1A is formed in the same cylindrical shape as the coupling portion 16A of the outer cylinder 1A. A stopper 50 made of rubber is liquid-tightly sealed in the front chamber outer cylinder. A distance P from an end opening 17 to the stopper 50 is set longer than a distance Q from a bypass groove 3 to the end face of a plunger 7 at the side of the bypass groove 3. A bottomed cylindrical hollow end housing 51 is made of plastic, with elasticity. An end 53 of the cylindrical end 5 is gas-tightly sealed in a coupling portion 52 of the housing 51. A columnar space from the end opening 17 of the end 5 to an inner surface 56 of a bottom 55 of the housing 51 is formed as a bypass chamber 57. The bypass chamber 57 has a length R set greater than the thickness S of the stopper 50. A diameter T of the bypass chamber 57 is set the same as the inner diameter U of the end opening 17. The center of the diameter T coincides with the center of the inner diameter U. A sectional circular flat surface of the bypass chamber 57 contacts and coincides with the end opening 17. In the end housing 51, four bypasses 59 are recessed longitudinally on a housing inner wall 58 for forming the bypass chamber 57. A bottom groove 60 connected to the bypasses 59 is radially recessed on the inner surface 56 of the housing bottom 55. A housing recess 61 is formed at the center of the inner surface 56, where all the bottom grooves 60 are concentrated so that all the bottom grooves 60 are connected to the housing recess 61. An inverted frustoconical needle mounting portion 63 extends from the outer surface 62 of the housing bottom 55. A small hole 64 is perforated through from a frustum face 66 to the housing recess 61 in the needle mounting portion 63. An outer peripheral surface of the needle mounting portion 63 is gradually reduced in diameter toward its end as a luer tapered surface 26. A bottomed hollow cap 65, made of plastic, with elasticity, is tapered in the same taper as the luer tapered surface 26 of the needle mounting portion 63 on the inner wall surface of the hollow section. The needle mounting portion 63 is liquid-tightly sealed in the hollow section.

Figure 7:
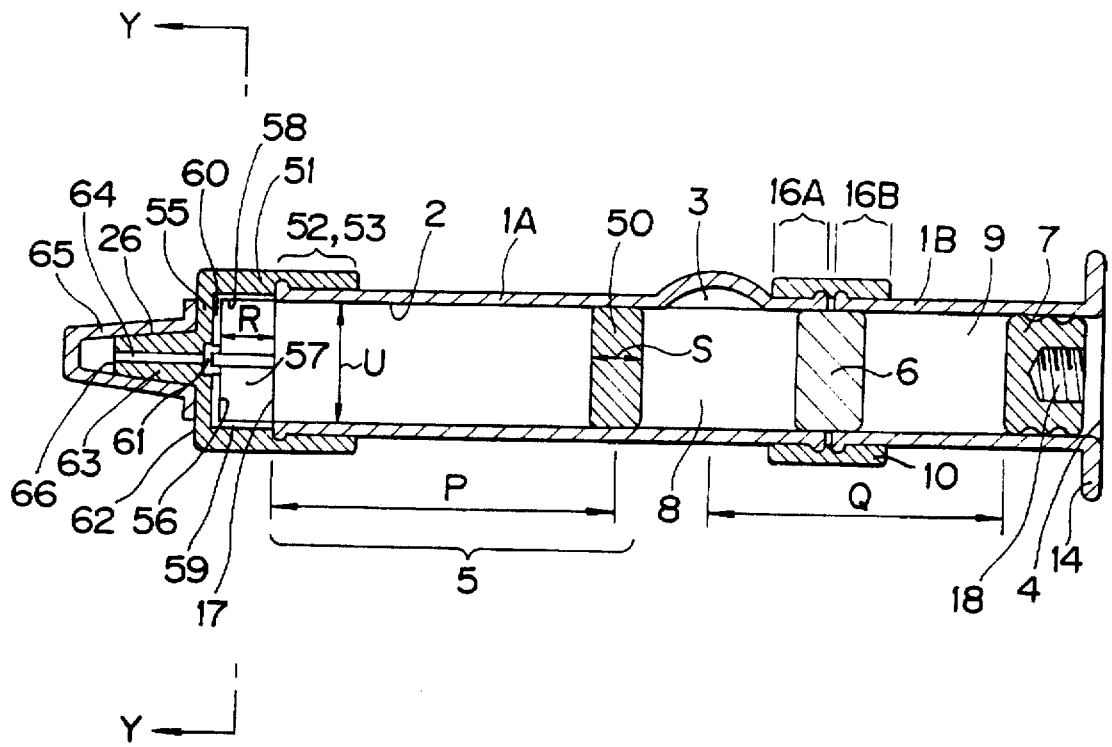
FIG. 7 is a longitudinal sectional view of a third embodiment according to the present invention.
Figure 8:
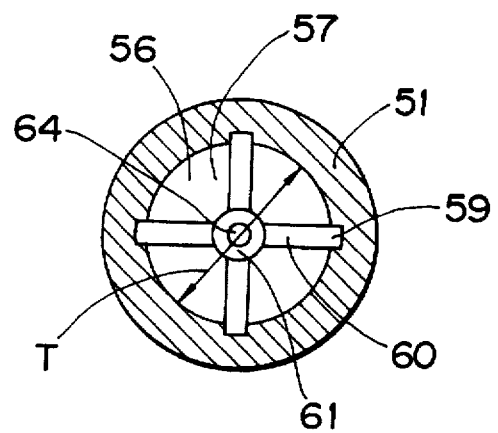
FIG. 8 is a sectional view taken along line Y—Y of FIG. 7.

Since the third embodiment shown in FIG. 7 is formed in a structure of the cylindrical end 5 as described above, the needle mounting portion 63 can be held in a sterilized state by the cap 65. This is performed by sterilizing, such as thermally sterilizing, the front chamber outer cylinder 1A before powdered medicine is sealed in the outer cylinder 1A. The interior of the small hole 64 of the needle mounting portion 63, the bypass chamber 57 and the interior of the cylindrical end 5, from the stopper 50 to the end opening 17, can be sealed in a sterilized state.

Figure 9:
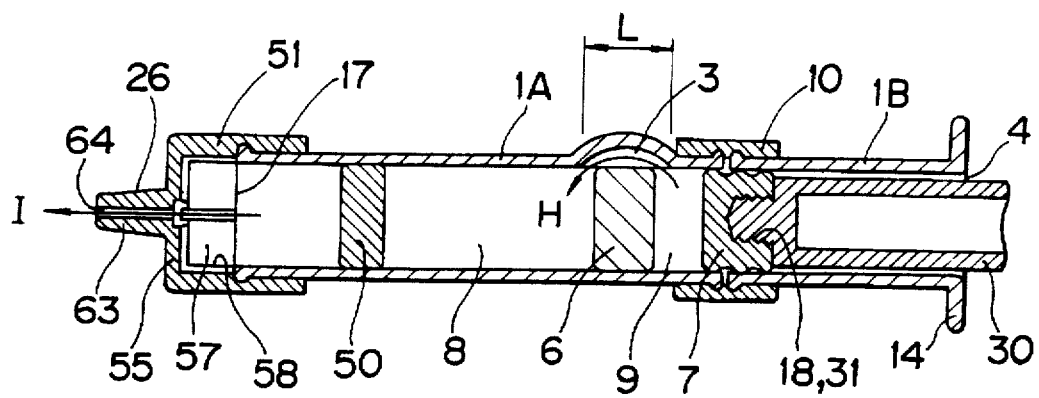
FIG. 9 is a longitudinal sectional view showing initial pressing of a plunger of the FIG. 7 device.
Figure 10:
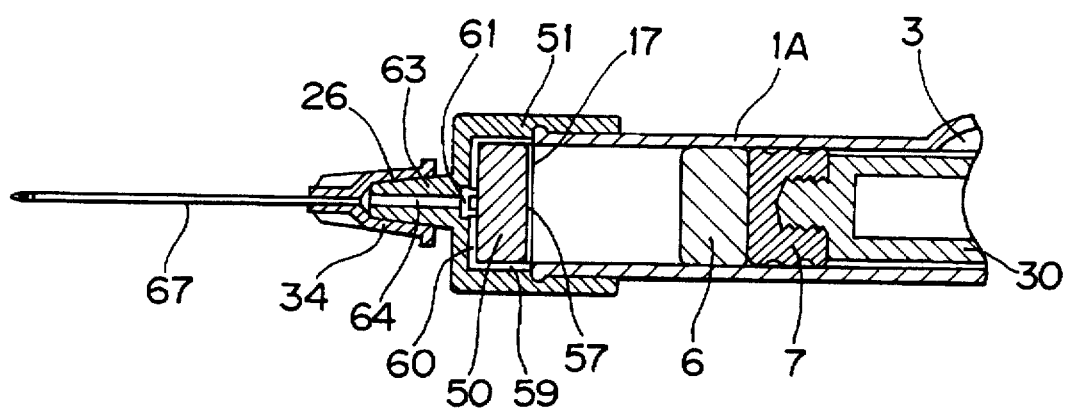
FIG. 10 is a partial longitudinal sectional view showing a syringe needle mounted in the device of FIG. 7.

Powdered medicine is sealed in a sterilized state in a first inner chamber 8 between the stopper 50 and the sealing plug 6. Liquid medicine is sealed in a sterilized state in a second inner chamber 9 between the sealing plug 6 and the plunger 7. For injection, as shown in FIG. 9, the cap 65 is removed, and the plunger 7 is pressed forward by the syringe inner cylinder 30. Thus, the hydraulic pressure of the liquid medicine is raised by pressing the plunger 7, and the sealing plug 6 is pressed forward by the raised hydraulic pressure. The air in the second inner chamber 9 is compressed by pressing the sealing plug 6 to raise pneumatic pressure in the second inner chamber 9, so that the stopper 50 is pressed forward by the raised pneumatic pressure. Since the cap 65 is removed, the bypass chamber 57 communicates with the atmosphere. Therefore, even if the stopper 50 is pressed forward, the air in the cylindrical end 5 escapes into the atmosphere, as indicated by an arrow I in FIG. 9, and hence the internal pressure of the bypass chamber 57 is not raised. Thus, the sealing plug 6 is smoothly pressed forward to the bypass groove 3 side. When the sealing plug 6 is moved to a range of the length L of the bypass groove 3, the first inner chamber 8 communicates with the second inner chamber 9 through the bypass groove 3. Then, the sealing plug 6 is stopped and only the plunger 7 is thereafter continuously pressed forward to feed the liquid medicine into the first inner chamber 8. When the plunger 7 reaches the sealing plug 6, the entire quantity of the liquid medicine is fed into the first inner chamber 8. The powdered medicine and the liquid medicine are then mixed in the first inner chamber 8 to produce a parenteral solution.

The stopper 50 is also pressed forward by pressing the plunger 7. Since a distance P from the end opening 17 of the cylindrical end 5 to the stopper 50 is set longer than a distance Q from the bypass groove 3 to the end face of the plunger 7 at the bypass groove 3 side, the stopper 50 is not pressed forward into the interior of the bypass chamber 57 until the entire quantity of the liquid medicine is fed to the first inner chamber 8. After the parenteral solution is produced and the plunger 7 is further pressed forward, the stopper 50 is pressed forward into the bypass chamber 57. When the stopper 50 is introduced into the bypass chamber 57, the stopper 50 contacts the housing bottom 55 of the end housing 51. However, the parenteral solution is not blocked by the stopper 50, but is fed from the bypasses 59 of the housing inner wall 58 through the bottom groove 60 to the housing recess 61, is further fed to the small hole 64 of the needle mounting portion 63 perforated to the housing recess 61, and is fed out of the dual chamber prefillable syringe. When the sealing plug 6 contacts the stopper 50, the entire quantity of the parenteral solution is exhausted.

In the third embodiment shown in FIG. 7, the needle base 34 of the syringe needle 67 is mounted on the luer tapered surface 26 of the needle mounting portion 63, and the syringe needle 67 is mounted at the needle mounting portion 63. The syringe 67 is not constituted such that the bottom 21 of the sealing plug 20 is pierced by the short needle 33 of the double flank syringe needle 32, as in the embodiment shown in FIG. 4.

In the third embodiment shown in FIGS. 7 to 10, the shape and materials are not limited to the above-described shape and materials. In this third embodiment, the coupling component 10 is formed of one piece. However, the coupling component 10 is not limited to the one piece structure and may be divided.

Figure 11:
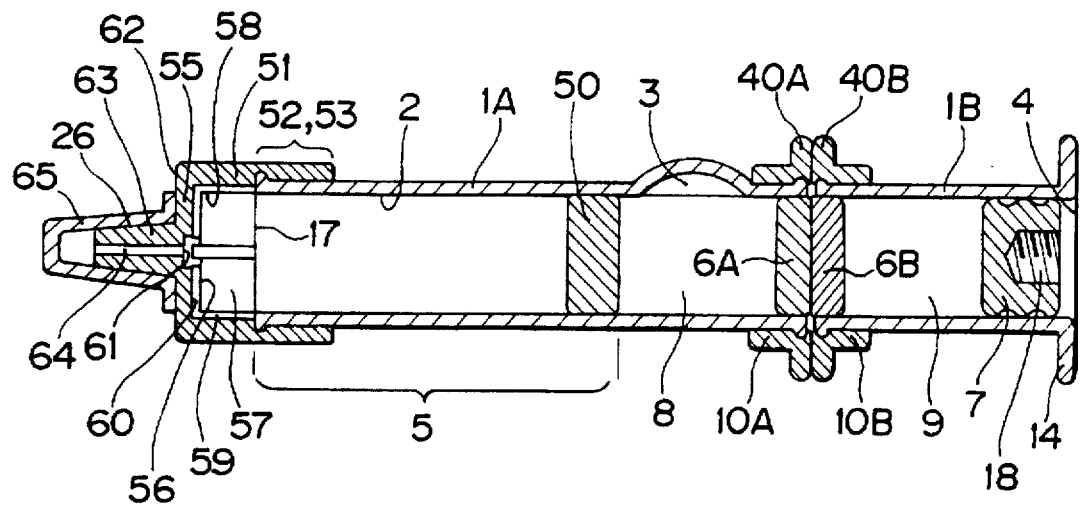
FIG. 11 is a longitudinal-sectional view of a fourth embodiment according to the present invention.

The fourth embodiment according to the present invention will be described with reference to FIG. 11. The structure, operation and effect of the embodiment shown in FIG. 11 are all included in the second embodiment shown in FIGS. 5 and 6 and the third embodiment as shown in FIGS. 7 to 10, and already described, and the description will be omitted. The reference numerals and symbols of the further embodiment shown in FIG. 11 are the same as those of the two embodiments shown in FIGS. 7 to 10.

The fifth embodiment according to the present invention will be described with reference to FIG. 12. In comparison with the third embodiment as shown in FIGS. 7 to 10, the same device and components are denoted by the same reference numerals and symbols, and only different structure, operation and effect will be described.

Figure 12:
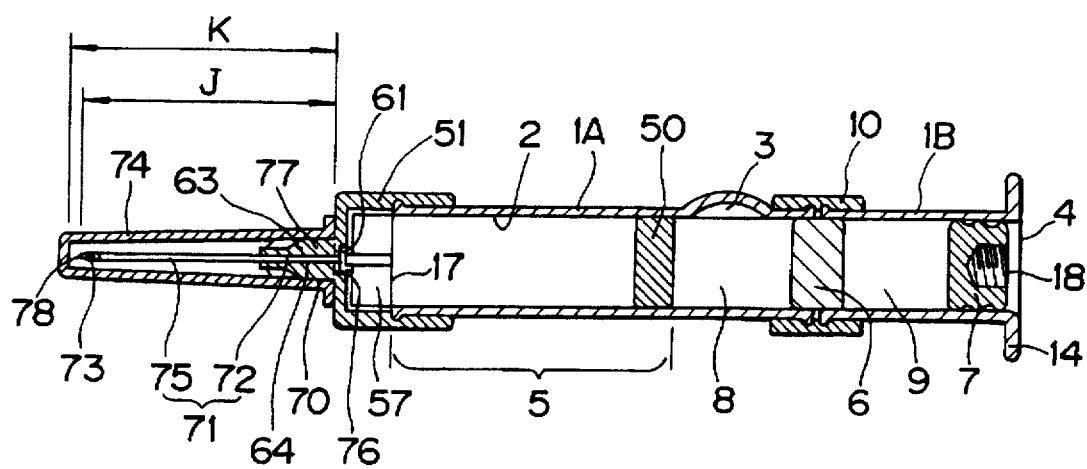
FIG. 12 is a longitudinal sectional view of a fifth embodiment according to the present invention.

In the embodiment shown in FIG. 12, an outer wall surface of a base 77 of the needle mounting portion 63 is gradually reduced in diameter toward its end to form a tapered surface 70. The taper of the tapered surface 70 is not limited to a luer taper. A needle base 72 of a needle tube 71 is perforated through from the end of the small hole 64 of the needle mounting portion 63 to the housing recess 61. The needle base 72 is gas-tightly secured to the needle mounting portion 63. A needle hole 73, perforated longitudinally of the needle tube 71, is connected to the housing recess 61. An end needle 75 of the needle tube 71 protrudes from the needle mounting portion 63. A needle guard 74 of a cap is made of plastic having elasticity and formed in a bottomed hollow shape. A length K of a hollow section of the needle guard 74 is set longer than the total length J of the end needle 75 and the needle mounting portion 63. The inner wall surface of the hollow section of the needle guard 74 is formed in a taper the same as tapered surface 70 of the base 77 of the needle mounting portion 63. An opening 76 of the needle guard 74 is liquid-tightly sealed by the base 77 of the needle mounting portion 63, to seal the end needle 75 of the needle tube 71 with the hollow section.

In the embodiment shown in FIG. 12, since the needle tube 71 is mounted at the needle mounting portion 63, mounting a syringe needle at the needle mounting portion 63 is eliminated. Since this embodiment has the above-described structure, the end needle 75 of the needle tube 71, the needle mounting portion 63, the interior of the needle hole 73 of the needle tube 71, a bypass chamber 57 in the end housing 51, and the interior of the cylindrical end 5 from the stopper 50 to the end opening 17 can be held in sterilized states by the needle guard 74. This is done by sterilizing, (e.g. thermally) the front chamber outer cylinder 1A before powdered medicine is sealed in the outer cylinder 1A. Further, the end needle 75 is protected by the needle guard 74 to prevent the deformation of the end needle end 78. Also, pain imparted to a patient at the time of injection is eliminated or reduced.

In the embodiment shown in FIG. 12, the shape and materials are not limited to the above-described shape and materials. Although the coupling component 10 is formed of one piece in the embodiment shown in FIG. 12, the coupling component 10 is not limited to the one piece structure, but may be divided.

Figure 13:
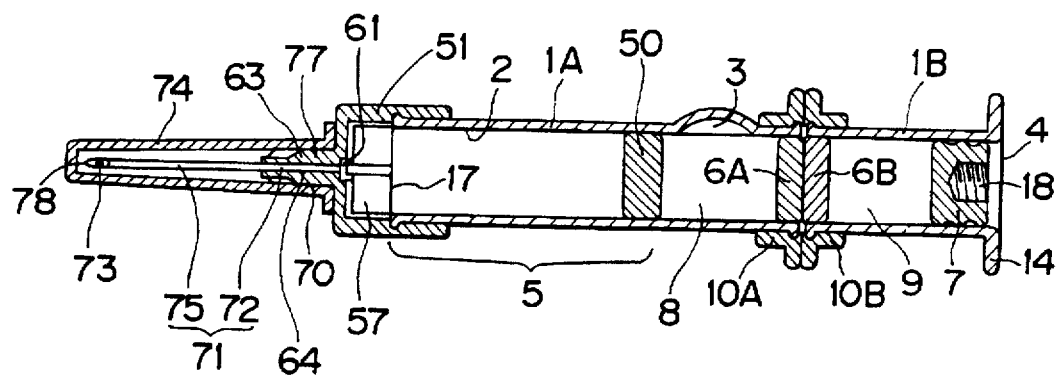
FIG. 13 is a longitudinal sectional view of a sixth embodiment according to the present invention.

The sixth embodiment according to the present invention will be described with reference to FIG. 13. The structure, operation and effect of the embodiment shown in FIG. 13 are all included in the second embodiment shown in FIGS. 5 and 6 and the fifth embodiment as shown in FIG. 12, and already described, and the description will be omitted. The reference numerals and symbols of the further embodiment shown in FIG. 13 are the same as those of the two embodiments shown in FIGS. 5, 6 and FIG. 12.

The seventh embodiment according to the present invention will be described with reference to FIGS. 14 to 17. In comparison with the third embodiment as shown in FIGS. 7 to 10, the same device and components are denoted by the same reference numerals and symbols, and only different structure, operation and effect will be described.

Figure 16:
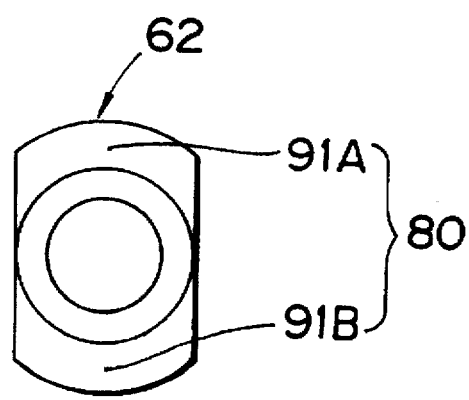
FIG. 16 is an enlarged left side view of a cap of FIG. 14.

A luer lock 86 is suspended on the outer surface 62 of a housing bottom 55 of an end housing 51. The luer lock 86 is made of plastic, has a cylindrical shape, and includes a columnar portion 85 which includes the needle mounting portion 63 therein. Two stripes of threads, female threads 88A and female threads 88B, are circumferentially formed and deviated at 180 degrees on the inner peripheral surface of the columnar portion 85 to form female threads 88. As shown in FIG. 16, a rectangular flange 80 including a collar 91A and collar 91B is formed at the end of the outer wall surface of the cap 65 at the cap opening 68 side. The collar 91A of the flange 80 is engaged with the female threads 88A of the luer lock 86 and the collar 91B of the flange 80 is engaged with the female threads 88B of the luer lock 86, so that the cap 65 is held by the luer lock 86. Also, this results in the needle mounting portion 63 being liquid-tightly sealed in the hollow section of the cap 65.

Figure 14:
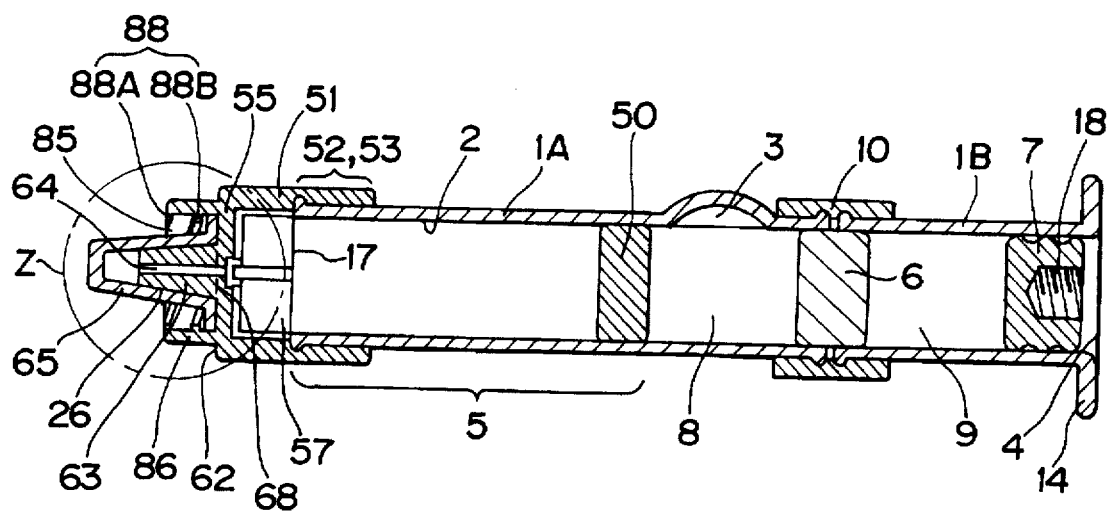
FIG. 14 is a longitudinal sectional view of a seventh embodiment according to the present invention.
Figure 15:
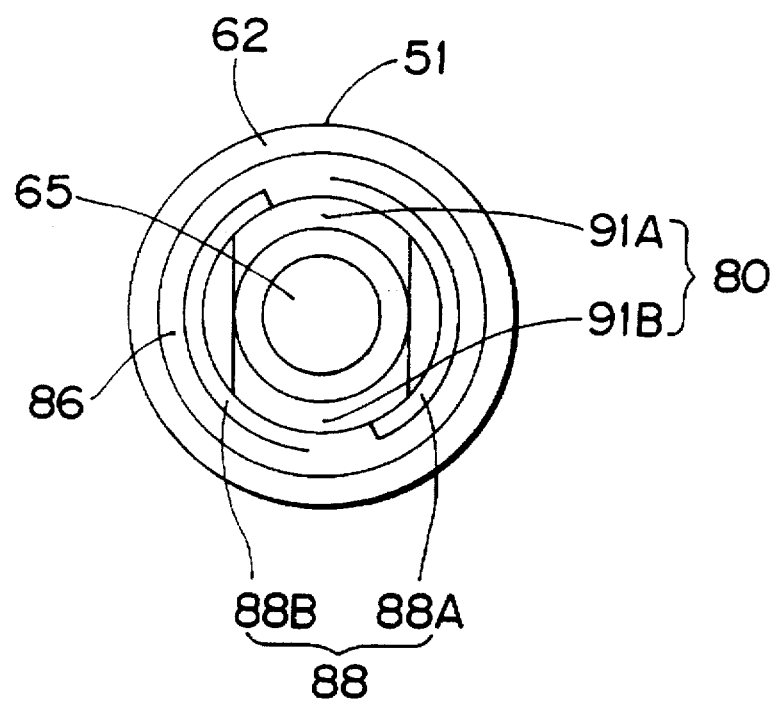
FIG. 15 is an enlarged left side view of a portion z of FIG. 14.

Since the embodiment shown in FIG. 14 has the above-described structure, the sealing state of the needle mounting portion 63 with the cap 65 is held by the engagement of the flange 80 of the cap 65 with the female threads 88A and female threads 88B of the luer lock 86. Thus, there is no danger of the cap 65 being removed from the needle mounting portion 63 up to the time of injection. Therefore, the needle mounting portion 63, the interior of the small hole 64 of the needle mounting portion 63, the bypass chamber 57, and the interior of the cylindrical end 5, from the stopper 50 to the end opening 17, can be reliably held in a sterilized state by the cap 65 up to the time of injection.

Figure 17:
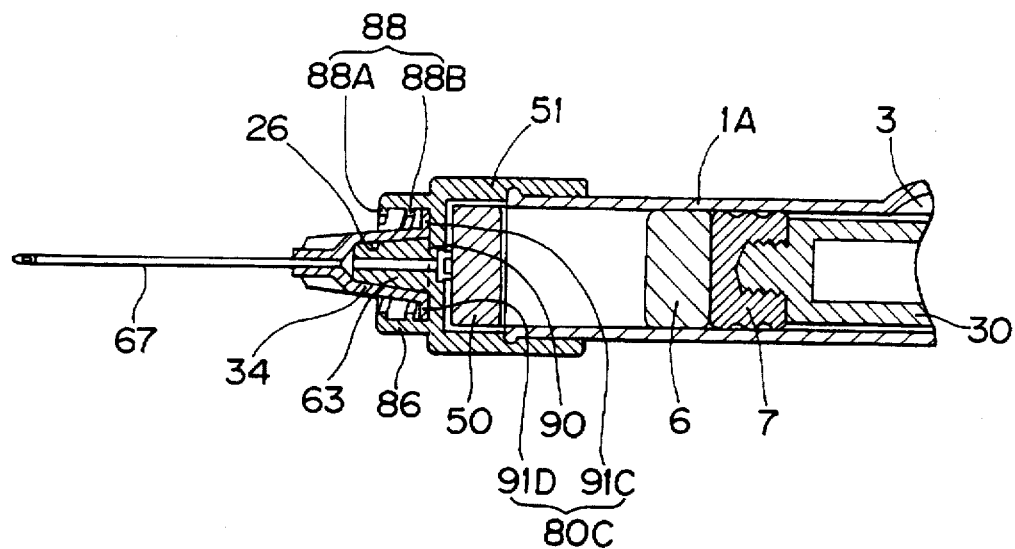
FIG. 17 is a partial longitudinal sectional view showing a syringe needle mounted in the FIG. 14 device.

In the case of injection, after the cap 65 is removed from the needle mounting portion 63, the needle base 34 of the syringe needle 67 is mounted at the needle mounting portion 63, as shown in FIG. 17. A rectangular flange 80C including a collar 91C and a collar 91D is formed at an end of the outer wall surface of the needle base 14 at a needle base opening 90 side. The flange 80C is engaged with the female threads 88 of the luer lock 86, and the needle base 34 can be mounted at the needle mounting portion 63. In this case, since the syringe needle 67 is held by the engagement of the flange 80C of the needle base 34 with the female threads 88A and female threads 88B of the luer lock 86, there is no danger of the syringe needle 67 being removed from the needle mounting portion 63 during injection.

In the embodiment shown in FIG. 14, the shape and materials are not limited to the above-described shape and materials. Further, the method of engaging the flange 80 of the cap 65 and the flange 80C of the needle base 34 with the female threads 88 of the luer lock 86 is not limited to the above-described method. In addition, while the coupling component 10 is formed of one piece, it is not limited to the one piece structure and may be divided.

Figure 18:
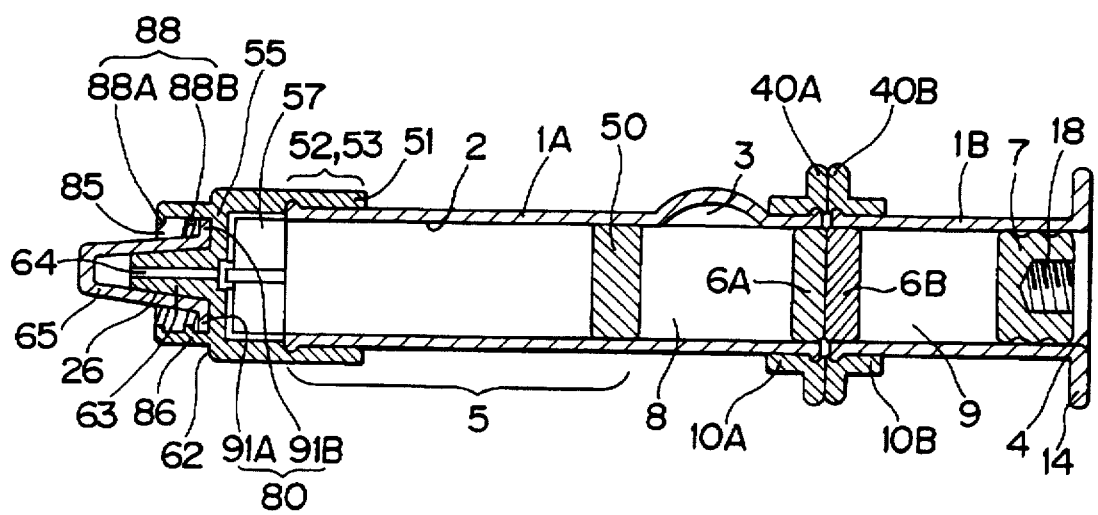
FIG. 18 is a longitudinal sectional view of an eighth embodiment according to the present invention.
Figure 19:
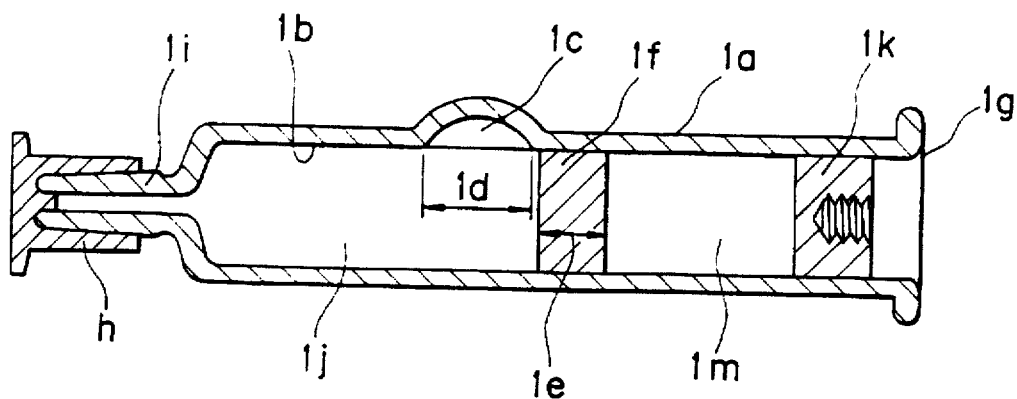
FIG. 19 is a longitudinal sectional view showing an example of prior art.
Figure 20:
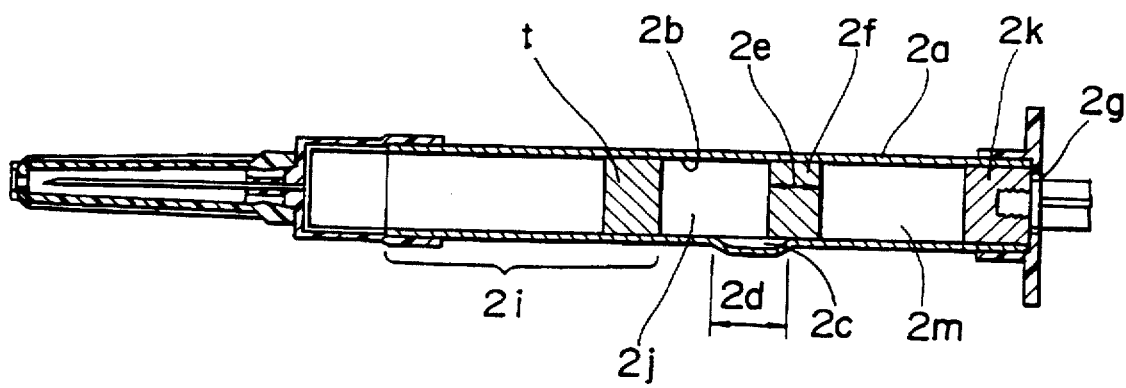
FIG. 20 is a longitudinal sectional view of another example of prior art.
Figure 21:
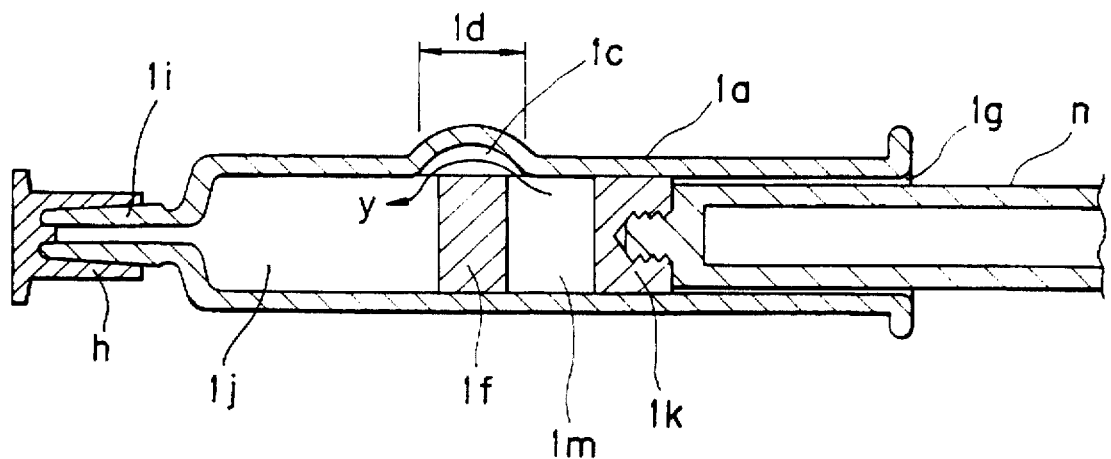
FIG. 21 is a longitudinal sectional view showing initial pressing of a plunger of the FIG. 19 device.

The eighth embodiment according to the present invention will be described with reference to FIG. 18. The structure, operation and effect of the embodiment shown in FIG. 18 are all included in the second embodiment shown in FIGS. 5 and 6 and the seventh embodiment as shown in FIGS. 14 to 17, and already described, and the description will be omitted. The reference numerals and symbols of the embodiment shown in FIG. 18 are the same as those of the embodiments shown in FIGS. 5, 6 and FIGS. 14 to 17.

In all the embodiments of the above-described assembling type dual chamber prefillable syringe, the descriptions have been made in such a manner that a predetermined quantity of the powdered medicine freeze-dried by the freeze-drying apparatus is sealed in a sterilized state in the first inner chamber 8, and a predetermined quantity of the liquid medicine of dissolved solution for dissolving the powdered medicine is sealed in a sterilized state in the second inner chamber 9. However, the medicine sealed in the first inner chamber 8 is not limited to the powdered medicine freeze-dried by the freeze-drying apparatus, and the medicine sealed in the second inner chamber 9 is not limited to the liquid medicine of dissolved solution for dissolving the powdered medicine. In other words, in the dual chamber prefillable syringe according to this invention, a predetermined quantity of powdered medicine or liquid medicine can be sealed in a sterilized state in the first inner chamber 8, and a predetermined quantity of liquid medicine can be sealed in a sterilized state in the second inner chamber 9. However, the effect of this invention is particularly realized in the case that a predetermined quantity of the powdered medicine, freeze-dried by the freeze-drying apparatus, is sealed in a sterilized state in the first inner chamber 8, and a predetermined quantity of the liquid medicine of dissolved solution for dissolving the powdered medicine is sealed in a sterilized state in the second inner chamber 9.

Since this invention is constituted in the structure and operated as described above, the following advantages are provided.

The powdered medicine and liquid medicine are separately sealed in a sterilized state in the first and second inner chambers. As the liquid medicine is fed into the first inner chamber without opening the sealing states of the first and second inner chambers, there is no danger of the parenteral solution being contaminated by bacteria, etc., at the time of producing the parenteral solution.

When the dual chamber prefillable syringe is assembled, the step of sealing the powdered medicine in a sterilized state in the front chamber outer cylinder and the step of sealing the liquid medicine in a sterilized state in the rear chamber outer cylinder can be treated in parallel. Therefore, the filling and sealing processes of the liquid medicine in the syringe outer cylinder, after the powdered medicine is sealed in a sterilized state, is eliminated, and there is no danger of the liquid medicine, powdered medicine and the interior of the syringe outer cylinder being contaminated by bacteria, etc.

Further, if the powdered medicine is sealed in a sterilized state in the front chamber outer cylinder, the production efficiency of the freeze-drying work by the freeze-drying apparatus is improved.

The first inner chamber can reliably communicate with the second inner chamber through the bypass groove, and assembly is facilitated.

When the dual chamber prefillable syringe is assembled, the first and second inner chambers are not opened. Therefore, there is no danger of the powdered medicine and the liquid medicine being contaminated by bacteria, etc.

The cylindrical end of the needle mounting portion can be reliably held in a sterilized state in the guard up to the time of injection. During injection, the guard is broken at the collapsible brittle portion to expose the head, and the double flank syringe needle can be mounted at the head.

The needle mounting portion, the interior of the small hole of the needle mounting portion, bypass chamber 57 and the interior of the cylindrical end from the stopper to the end opening can be held in a sterilized state.

When the cap is removed, the liquid medicine is fed to the first inner chamber through the bypass groove, and the powdered medicine and the liquid medicine are mixed in the first inner chamber to smoothly produce parenteral solution.

When the syringe needle is mounted at the needle mounting portion, the sealing plug is not collapsed by the syringe needle. Therefore, the needle hole of the syringe needle is not blocked by the collapsed pieces, and the pieces are not introduced into the patient together with the parenteral solution.

It is easy to mount the syringe needle at the needle mounting portion.

Mounting the syringe needle at the needle mounting portion is eliminated.

The end needle of the needle tube, the needle mounting portion, the interior of the needle hole of the needle tube, the bypass chamber and the interior of the cylindrical end, from the stopper to the end opening, can be held in a sterilized state by the needle guard.

Further, the end needle is protected by the needle guard to prevent deformation of the end needle end, and the danger of imparting pain to a patient due to the deformation of the end needle end can be obviated.

There is no danger of cap removal from the needle mounting portion up to the time of injection. Therefore, the needle mounting portion, the interior of the small hole of the needle mounting portion, the bypass chamber and the interior of the cylindrical end from the stopper to the end opening, are reliably held in a sterilized state by the cap up to the time of injection.

I claim:

1. A dual chamber prefillable syringe, comprising:
   a syringe outer cylinder having an inner wall and a recessed longitudinal bypass groove on the inner wall the bypass groove having a length, and the outer cylinder having an outer cylinder opening at one end thereof and an opposite cylindrical end having a liquid-tight seal;
   a sealing plug of thickness less than the length of said bypass groove, the sealing plug providing a liquid-tight seal between the outer cylinder and the sealing plug at a position between the outer cylinder opening and said bypass groove to form a first inner chamber between the outer cylinder end and said sealing plug; and
   a plunger disposed at a position between said outer cylinder opening and said sealing plug, the plunger forming a liquid-tight seal between the outer cylinder and the plunger and forming a second inner chamber between said plunger and said sealing plug;
   wherein:
   said syringe outer cylinder is split, in a direction perpendicular to a longitudinal direction of the outer cylinder and at a position between said outer cylinder opening and said bypass groove, dividing the outer cylinder into a front chamber outer cylinder and a rear chamber outer cylinder;
   said front chamber outer cylinder includes said bypass groove, said cylindrical end, an inner, longitudinally extending wall, and a first split opening;
   said rear chamber outer cylinder includes said outer cylinder opening, an inner, longitudinally extending wall, and a second split opening;
   an inner peripheral edge of said first split opening of said front chamber outer cylinder is opposed over its entire periphery to an inner peripheral edge of said second split opening of said rear chamber outer cylinder, so that said front chamber outer cylinder and said rear chamber outer cylinder are disposed in series;
   said front chamber outer cylinder and said rear chamber outer cylinder are held in a liquid-tight manner by a coupling component;
   said bypass groove of said front chamber outer cylinder is spaced from said first split opening of said front chamber outer cylinder; and
   said sealing plug simultaneously contacts an entire periphery of both 1) said inner, longitudinally extending wall of said rear chamber outer cylinder and 2) said inner, longitudinally extending wall of said front chamber outer cylinder.

2. The dual chamber prefillable syringe according to claim 1, further comprising a stopper made of an elastic material, a bottomed end housing having a coupling portion and a hollow section, and a bottomed hollow cap having an elasticity,
   wherein:
   the stopper is sealed in the cylindrical end of the front chamber outer cylinder to provide a liquid-tight seal in said cylindrical end between said stopper and said front chamber outer cylinder;
   a distance from an end opening of said cylindrical end to said stopper is longer than a distance from the bypass groove to an end face of the plunger nearest the bypass groove;
   the cylindrical end is engaged in a gas-tight manner within the coupling portion of the end housing, so that the hollow section of said end housing extends from the end opening of said cylindrical end to an inner surface of said end housing to form a bypass chamber;
   a length of said bypass chamber is longer than a thickness of said stopper;
   said end opening is included in a surface contacting said bypass chamber;
   a plurality of recessed longitudinal bypasses are formed on an inner wall of said end housing;
   a plurality of recessed radial bottom grooves coupled to said bypasses are formed on an inner surface of said end housing;
   a housing recess is formed on the inner surface of the bottom of said end housing, the bottom grooves all being connected to said housing recess;
   a needle mounting portion extends from an outer surface of said end housing, the needle mounting portion including a small hole extending from an end of the needle mounting portion to said housing recess; and
   the needle mounting portion is sealed in a liquid-tight manner with the hollow section of the bottomed hollow cap.

3. The dual chamber prefillable syringe according to claim 2, wherein:
   an outer wall surface of the needle mounting portion is gradually reduced in diameter toward its end to form a tapered surface; and
   an inner wall surface of the bottomed hollow cap is formed parallel to the tapered outer wall surface.

4. The dual chamber prefillable syringe according to claim 3, further comprising a lock having a columnar portion; wherein:

the lock extends from the outer surface of the bottom of the end housing;

the columnar portion includes the needle mounting portion therein;

female threads are formed on an inner peripheral surface of the columnar portion;

a flange is formed on an outer wall surface of the cap; and the flange is secured to the lock by the female threads.

5. The dual chamber prefillable syringe according to claim 2, further comprising a needle tube and a cap; wherein:

an outer wall surface of the needle mounting portion is gradually reduced in diameter toward its end to form a tapered surface;

a base needle of a needle tube extends from the end of the small hole of the needle mounting portion to the housing recess, so that said base needle is secured in a gas-tight manner to the small hole of the needle mounting portion;

said needle tube includes a needle hole extending through said needle tube and connected to said housing recess;

an end needle of said needle tube protrudes from the needle mounting portion;

the cap acts as a needle guard;

a length of a hollow section of said needle guard is longer than a total length of said end needle and the needle mounting portion;

an inner wall of said needle guard is formed parallel to the tapered surface of the needle mounting portion; and the end needle is sealed in the hollow section of said needle guard.

6. The dual chamber prefillable syringe according to claim 1, wherein said sealing plug is formed of one piece.

7. The dual chamber prefillable syringe according to claim 1, wherein:

said sealing plug comprises a first sealing plug member and a second sealing plug member, the sealing plug being split in a direction perpendicular to a direction of thickness of said sealing plug;

said first sealing plug member provides a liquid-tight seal between the first sealing plug member and the front chamber outer cylinder, at a position near the first split opening of the front chamber outer cylinder;

said second sealing plug member provides a liquid-tight seal between the second sealing plug member and the rear chamber outer cylinder, at a position near the second split opening of the rear chamber outer cylinder; and a distance from a first sealing plug member end face nearest the bypass groove to a second sealing plug member end face nearest the outer cylinder opening is shorter than the length of said bypass groove.

8. The dual chamber prefillable syringe according to claim 1, further comprising:

a) a needle mounting cylinder, including a base cylinder and an end cylinder, b) a bottomed hollow guard, and c) a bottomed hollow sealing plug made of an elastic material, wherein:

the bottomed hollow sealing plug is sealed in said cylindrical end in such a manner that a bottom of the bottomed hollow sealing plug faces the first inner chamber, forming said liquid-tight seal at the cylindrical end;

the base cylinder of the needle mounting cylinder is seated in a hollow section of said bottom hollow sealing plug;

the end cylinder of the needle mounting cylinder protrudes from an end opening of said cylindrical end;

an outer peripheral surface of the end cylinder is gradually reduced in diameter toward its end to form a tapered surface;

a cylindrical hole extends through the needle mounting cylinder from an end face of the end cylinder to an end face of said base cylinder;

a guard base of the bottomed hollow guard is secured in a gas-tight manner to an outer wall of said cylindrical end so that the end cylinder of said needle mounting cylinder is sealed in said guard; and the hollow guard includes a collapsible brittle portion, circumferentially formed about a widest diameter portion of said tapered surface of said end cylinder.

* * * * *